US005756859A

United States Patent [19]

McCloskey et al.

[11] Patent Number: 5,756,859

[45] Date of Patent: May 26, 1998

[54] METHOD FOR PREPARING AND PURIFYING 1,1,1-TRIS(4-HYDROXYPHENYL)ETHANE

[75] Inventors: Patrick Joseph McCloskey, Watervliet, N.Y.; Paul Dean Sybert, Evansville, Ind.; Julia Lam Lee, Schenectady; David Michel Dardaris, Ballston Spa, both of N.Y.

[73] Assignee: General Electric Company, Schenectady, N.Y.

[21] Appl. No.: 760,357

[22] Filed: Dec. 4, 1996

Related U.S. Application Data

[60] Provisional application No. 60/032,802, Jan. 5, 1996.

Related U.S. Application Data

[63] Continuation-in-part of Ser. No. 718,287, Sep. 20, 1996, abandoned.

[51] Int. Cl.$^{6}$ .................... C07C 39/12

[52] U.S. Cl. .................... 568/720

[58] Field of Search .................... 568/720, 722, 568/724, 717

[56] References Cited

U.S. PATENT DOCUMENTS 5,463,140 10/1995 Wehmeyer .

*Primary Examiner*—Gary Geist
*Assistant Examiner*—Karl J. Puttlitz, Jr.
*Attorney, Agent, or Firm*—William H. Pittman

[57] ABSTRACT

1,1,1-Tris(4-hydroxyphenyl)ethane in admixture with bisphenol A is obtained by the reaction of 2,4-pentanedione with excess phenol under acidic conditions and in the presence of a mercapto compound as promoter. The products may be separated by extracting bisphenol A with a chlorinated alkane. Purification of the resulting 1,1,1-tris(4-hydroxyphenyl)ethane is achieved by slurrying in and/or recrystallization from methanol-water, optionally with addition of an alkali metal borohydride or dithionite.

20 Claims, No Drawings

METHOD FOR PREPARING AND PURIFYING 1,1,1-TRIS(4-HYDROXYPHENYL)ETHANE

CROSS-REFERENCE TO RELATED APPLICATIONS

This application is a continuation-in-part of application Ser. No. 08/718,287, now abandoned filed Sep. 20, 1996 and claims priority from provisional application Ser. No. 60/032802 filed Jan. 5, 1996.

BACKGROUND OF THE INVENTION

This invention relates to the preparation and purification of branching agents for polycarbonates, and more particularly of 1,1,1-tris(4-hydroxyphenyl)ethane, hereinafter sometimes "THPE".

THPE, disclosed in U.S. Pat. Nos. 3,579,542 and 4,992,598, is in common use as a branching agent for polycarbonates. As such, it may be incorporated in reaction mixtures also containing dihydroxyaromatic compounds such as bisphenol A and carbonate sources such as phosgene or diphenyl carbonate.

THPE is commonly prepared by the reaction of 4-hydroxyacetophenone with phenol, said reaction being analogous to the reaction of phenol with acetone to form 2,2-bis(4-hydroxyphenyl)propane (hereinafter "bisphenol A"). As shown in U.S. Pat. No. 4,992,598, the product may be purified by washing with and/or recrystallizing from a methanol-water mixture, preferably with the addition of a decolorizing amount of sodium borohydride. This method is economically undesirable because of the high price of 4-hydroxyacetophenone. Therefore, it is of interest to develop a less expensive method for THPE production.

According to Japanese Kokai 53/141,250, the reaction of diones such as 2,4-pentanedione with excess phenol under acidic conditions and in the presence of a mercapto compound as promoter affords 2,2,4,4-tetrakis(4-hydroxyphenyl)pentane, in a reaction in all respects analogous to the aforementioned preparation of bisphenol A.

SUMMARY OF THE INVENTION

It has been discovered that the reaction between 2,4-pentanedione and phenol described in the aforementioned Japanese Kokai, at least under proper conditions, does not yield the described tetraphenol but rather THPE and bisphenol A. Thus, these compounds may be recovered and separated for further use. High yields of THPE are obtained.

Accordingly, a first aspect of the invention is a method for preparing THPE which comprises:

heating, at a temperature in the range of about 30°–100° C., a mixture of phenol and 2,4-pentanedione under acidic conditions and in the presence of an effective amount of a mercapto compound as promoter, the molar ratio of phenol to 2,4-pentanedione being at least about 6:1, to produce a mixture of bisphenol A and said THPE; and separating said THPE from said bisphenol A.

A second aspect is a method for preparing and purifying THPE which comprises the above heating step and, in addition:

combining the bisphenol A-THPE mixture with a chlorinated alkane in an amount to produce a precipitate of a THPE-bisphenol A mixture enriched in THPE, and isolating said precipitate;

contacting said precipitate with a methanol-water mixture containing at least 40% methanol by volume, said methanol-water mixture being previously saturated with THPE, to produce a THPE slurry, and recovering purified THPE from said slurry.

DETAILED DESCRIPTION; PREFERRED EMBODIMENTS

In the first aspect of the method of this invention, phenol and 2,4-pentanedione are employed in a molar ration of at least about 6:1. Higher molar ratios, typically at least about 8:1, afford particularly high yields, and ratios above about 11:1 are frequently advantageous since the reaction mixture then remains at least partially liquid at room temperature, facilitating handling and purification of the products. At lower ratios, the reaction mixture, while liquid at temperatures on the order of 40° C., solidifies at temperatures approaching 25° C.

The phenol and 2,4-pentanedione are blended in a molar ratio of at least about 6:1 under acidic conditions. Blending may be in any order; it is frequently advantageous to introduce the 2,4-pentanedione last and incrementally (e.g., dropwise) in order to maintain the phenol in large excess at all times. While a solvent may be employed, it is usually neither necessary nor preferred.

The acidic conditions may be provided by the addition of any acidic material, especially a relatively volatile material such as hydrogen chloride. Typically, hydrogen chloride gas is passed through the mixture during the reaction. It is also within the scope of the invention to introduce aqueous acid, either as a replacement for or in addition to the gaseous acidic material.

Also present as a promoter is a mercapto compound; that is, an organic compound having a —SH moiety. Relatively non-volatile mercapto compounds are preferred, with mercaptocarboxylic acids such as 3-mercaptopropionic acid and 2-mercaptoacetic acid being especially useful. Said mercapto compound is present in an effective amount to serve as a promoter, most often in the range of about 1–5% by weight based on phenol.

The reaction temperature is typically about 30°–100° C., preferably about 30°–60° C. During the reaction, THPE and bisphenol A separate as solids in a weight ratio on the order of 1:1, whereupon the mixture may become very viscous.

In the final preparation step, the THPE and bisphenol A are separated. A convenient means of separation is to remove bisphenol A by extraction with a chlorinated alkane such as methylene chloride or 1,2-dichloroethane. The major proportion of said bisphenol A can be recovered by evaporation of the chlorinated alkane. The weight ratio of THPE to bisphenol A in the extraction residue is typically on the order of 94:6. If essentially complete separation of THPE from bisphenol A is desired, at least two treatments with the chlorinated alkane may be employed. Small proportions of unreacted phenol, most often up to about 1% by weight of total crude product, are generally also present in the residue.

When 2,5-hexanedione and phenol are made to react under essentially similar conditions to those described herein, the product is 2,2,5,5-tetrakis(4-hydroxyphenyl) hexane, as expected from the aforementioned Japanese Kokai 53/141,250. Therefore, the fact that THPE and bisphenol A are the products obtained under those conditions from 2,4-pentanedione is extremely unexpected.

The second aspect of the invention includes several steps for purifying the product THPE. The first purification step, which takes place upon completion of the reaction between 2,4-pentanedione and phenol as described hereinabove, is combination of the crude product, most often a mixture of THPE and bisphenol A with a small proportion of unreacted phenol, with the aforementioned chlorinated alkane, most often methylene chloride. A sufficient quantity of methylene chloride is generally a volume ratio to crude product of at least about 2.5:1 and most often about 3:1. Prior or subsequent to methylene chloride addition, the crude product may be neutralized by addition of a basic reagent such as sodium hydroxide or sodium bicarbonate.

Upon preparing the combination with the chlorinated alkane, a THPE-enriched mixture of THPE and bisphenol A (hereinafter "enriched mixture") precipitates and can be isolated. This enriched mixture may contain as much as about 98% by weight THPE, with the balance being predominantly bisphenol A.

Conversion of the crude product to the enriched mixture is accompanied by a substantial decrease in color. Most often, the APHA color number of the crude product is about 2000 or greater, while that of the enriched mixture is on the order of 1000. For use as a branching agent for polycarbonates, however, an essentially colorless product having a color number of 150 or less is generally required. Since further purification and decolorization cannot be achieved by repeated washings with chlorinated alkane, further purification steps are necessary.

In the first further purification step, the enriched mixture is contacted with a methanol-water mixture containing at least 40% methanol by volume. It has been found that when the volume of methanol in the methanol-water mixture is less than 40%, a substantial amount of bisphenol A, typically greater than 2% by weight, remains in the product. Most often, the proportion of methanol in the methanol-water mixture is on the order of 42–50% by volume. To suppress dissolution of THPE in the methanol-water mixture, said mixture is saturated with THPE prior to use. The methanol-water mixture so saturated is hereinafter sometimes designated "wash liquid".

Contact between the wash liquid and the enriched mixture may be by slurrying or simply by washing. Typical contact temperatures are in the range of about 25°–50° C. The wash liquid may further contain a decolorizing proportion, most often about 0.01–0.10% by weight, of an alkali metal borohydride or dithionite, preferably sodium borohydride ($NaBH_4$) or sodium dithionite ($Na_2S_2O_3$). Sodium borohydride is preferred.

When contact is by slurrying, purified THPE is recovered by filtration, most often preceded by cooling to about 25° C. if a higher temperature has been employed to produce the slurry, from the THPE slurry thus obtained. The purified THPE produced in this step is generally at least 98% pure, with bisphenol A being the only impurity present in substantial amount.

The methanol-water filtrate recovered from the purified THPE is itself THPE-saturated. Therefore, it may be recycled for use as wash liquid with further enriched mixture.

The purified THPE obtained from the above-described purification method is generally of a light cream color. It may be converted to essentially pure white product by dissolution in methanol and treatment with a decolorizing proportion of alkali metal borohydride or dithionite. The initially amber solution turns pale yellow upon such treatment. It may be filtered and maintained at a temperature in the range of 25°–50° C., after which water at the same temperature may be added slowly with stirring and the solution cooled if necessary to ambient temperature, resulting in the precipitation of essentially pure THPE as a white solid.

When contact between wash liquid and the enriched mixture is by washing rather than slurrying, as by spraying the filter cake with the wash liquid, the enriched mixture thus obtained may have a somewhat higher bisphenol A content, often up to about 5% by weight. It may then be further contacted as described hereinabove with methanol containing a decolorizing proportion of alkali metal borohydride or dithionite, and, optionally, also with decolorizing charcoal. After filtration if necessary, the resulting solution may be combined with water to precipitate a final product which generally comprises at least about 97% THPE, with the balance being bisphenol A. The presence of bisphenol A in such proportions is tolerable when the product is to be used as a polycarbonate branching agent.

The invention is illustrated by the following examples. All percentages are by weight unless otherwise indicated.

EXAMPLE 1

A 500-ml round-bottomed flask equipped with a stirrer was charged with 100 g (1.06 mole) of phenol, 1.50 g (14 mmol) of 3-mercaptopropionic acid and 100 mg of p-terphenyl as an internal standard. The reaction mixture was warmed to 60° C., whereupon the phenol melted. Hydrogen chloride gas was bubbled through the mixture for 30 minutes, after which it was cooled to 40° C. and 8.33 g (88.3 mmol) of 2,4-pentanedione was added dropwise over 30 minutes. Heating at 40° C. was continued with occasional addition of hydrogen chloride gas, during which time the mixture became very viscous and a precipitate slowly formed. Stirring at room temperature was continued for 24 hours.

A portion of the mixture was filtered, yielding an orange solid shown by analysis to be a mixture of THPE and bisphenol A. To the remainder of the mixture was added 300 ml of methylene chloride, whereupon a pink solid precipitated and was collected by filtration. Liquid chromatographic analysis showed the solid to be an approximately 95:5 mixture of THPE with bisphenol A. Upon reextraction with methylene chloride, there was obtained a light orange solid which was shown to be THPE containing only about 1–2% bisphenol A. The total crude yield of THPE was about 49.5% of theoretical.

Upon evaporation of the methylene chloride, bisphenol A was obtained in a yield of about 50–60%.

EXAMPLES 2–7

The procedure of Example 1 was repeated, with parameters including the molar ratio of phenol to 2,4-pentanedione, the promoter proportion, the temperature and the reaction time being varied. The results are listed in Table I.

TABLE I

| Example | Molar ratio, phenol:pentanedione | Promoter, mole percent** | Temperature, °C. | Time, hrs. | THPE yield, % |
|---|---|---|---|---|---|
| 2 | 6:1 | 3.0 | 60–RT | 24 | 48 |
| 3 | 8:1 | 1.5 | 40 | 40 | 49 |
| 4 | 8:1 | 1.5 | 60–RT | 64 | 59 |
| 5 | 9:1 | 1.5 | 60–RT | 30 | 52 |
| 6 | 10:1 | 1.5 | 60–RT | 48 | 59 |
| 7 | 12:1 | 3.0 | 60–RT | 72 | 61 |

*RT = Room temperature.
**Based on phenol.

EXAMPLE 8

A 250-ml round-bottomed flask equipped with a mechanical stirrer was charged with 94 g (1 mole) of phenol, 3.06 g (28.9 mmol) of 3-mercaptopropionic acid. 1.65 ml of 38% aqueous hydrogen chloride solution and 100 mg of p-terphenyl as an internal standard. The mixture was warmed to 60° C. to melt the phenol, after which hydrogen chloride gas was bubbled through the mixture for 30 minutes. It was then allowed to cool to room temperature and 8.33 g (83 mmol) of 2,4-pentanedione was added over 30 minutes. Hydrogen chloride passage was continued at room temperature for 8 hours, during which time the mixture became very viscous. Stirring was then continued for 40 hours.

Upon cessation of stirring, the reaction mixture solidified as a brownish-red mass. Methylene chloride, 150 ml, was added, resulting in separation of a pink precipitate which was removed by filtration. It was shown by liquid chromatographic analysis to be an approximately 95:5 mixture of THPE and bisphenol A. Further extraction of the filtrate with methylene chloride yielded a second crop shown to be a 90:10 mixture of THPE and bisphenol A. The total crude yield of THPE was 59.9%.

Upon concentration of the filtrate and addition of water, a reddish solid formed which was shown by analysis to 55% phenol, less than 5% THPE and 40% bisphenol A. The total yield of bisphenol A was about 50%.

EXAMPLE 9

A reaction product of phenol and 2,4-pentanedione was prepared by a reaction procedure similar to that described in the first part of Example 1, slurried in methylene chloride and filtered. The filtration residue was a light yellow-orange solid which had an APHA color number of 2144. It was found by liquid chromatographic analysis to comprise 93.4% THPE, 5.8% bisphenol A and 0.6% phenol.

A 100-gram sample of this crude material was slurried at 50° C. for 20 minutes in 300 ml of a water-methanol mixture comprising 58% water and 42% methanol by weight, which had been previously saturated with THPE. The slurry was allowed to cool to room temperature, with stirring, over 2 hours. The solids which separated were collected by filtration and analyzed; they were found to have an APHA color number of 1021 and to comprise 98.3% THPE and 1.7% bisphenol A.

EXAMPLE 10

Various portions (30 g each) of the product of Example 9 were dissolved in methanol and the resulting amber solutions were treated with 50 mg of sodium borohydride, as a result of which the solutions turned very pale yellow. The solutions were filtered and various proportions of water were added, with stirring, at 50° C. or at room temperature. The resulting cloudy solutions were stirred at room temperature for 2 hours, filtered and washed with 100 ml of a water-methanol solution comprising 70% water and 30% methanol by volume. The products were then dried at 40° C. under vacuum.

The results are given in Table II. Yields are based on the original 30-g sample.

TABLE II

| Run | Methanol, ml | Water, ml | Temp., °C. | Yield, % | THPE purity, % | APHA color no. |
|---|---|---|---|---|---|---|
| 1 | 50 | 60 | 25 | 82 | 99.2 | 149 |
| 2 | 50 | 70 | 25 | 70 | 99.1 | 118 |
| 3 | 45 | 60 | 25 | 77 | 99.1 | 123 |
| 4 | 60 | 60 | 25 | 86 | 99.3 | 94 |
| 5 | 60 | 60 | 50 | 85 | 99.7 | 78 |
| 6 | 60 | 70 | 50 | 89 | 99.3 | 86 |
| 7 | 60 | 80 | 50 | 91 | 99.1 | 80 |
| 8 | 60 | 90 | 50 | 92 | 99.0 | 85 |

It is apparent from Table II that THPE is obtained in slightly higher yield and with slightly less color if precipitation is carried out at 50° C. than if it is effected at 25° C. Product purity is approximately the same irrespective of temperature. In each run, the only detected impurity was bisphenol A.

EXAMPLE 11

The procedure of Example 9 was repeated, varying the water-methanol volume ratio. The results are given in Table III.

TABLE III

| Run | Water-methanol vol. ratio | Analysis THPE | BPA | Phenol | APHA color no. |
|---|---|---|---|---|---|
| 1 | 50:50 | 98.3 | 1.7 | — | 1021 |
| 2 | 58:42 | 99.4 | 0.6 | — | 1408 |
| 3 | 60:40 | 98.2 | 1.8 | — | 1204 |
| 4 | 70:30 | 97.2 | 2.6 | 0.22 | 1171 |
| 5 | 80:20 | 94.6 | 4.9 | 0.5 | 1392 |

It is apparent that products of substantially higher purity are obtained when the methanol-water mixture contains at least 40% methanol by volume. Color numbers do not appear to be substantially affected by the water-methanol ratio.

EXAMPLE 12

A glass-lined reactor was charged with 19 parts (200 mmol) of phenol and warmed to 50° C. in a nitrogen atmosphere. 3-Mercaptopropionic acid (0.285 part) and 0.019 part of p-terphenyl as an internal standard were added. The solution was saturated with gaseous hydrogen chloride and 2 parts (20 mmol) of 2,4-pentanedione was added. The solution was heated at 40° C. for 48 hours, whereupon the reaction was complete and conversion to THPE was shown by liquid chromatographic analysis to be 61%.

Methylene chloride was added to the mixture and the resulting slurry was stirred for 2 hours to precipitate the crude THPE. The slurry was filtered, washed with additional methylene chloride and dried to provide 3.43 parts of a light tan solid comprising 94% THPE (53% crude yield), 5.4% bisphenol A and 0.6% phenol.

The filter cake was washed with 13.9 parts of a water-methanol solution comprising 58% water and 42% methanol by volume, which had been previously saturated with THPE and which also contained 0.05% sodium borohydride. Analysis of the product after washing showed it to comprise 94.1% THPE and 4.9% bisphenol A.

The washed filter cake was dissolved in 6.9 parts of methanol and 0.001 part of sodium borohydride was added, reducing the color noticeably. There was then added 0.0015 part of decolorizing carbon. The solution was stirred for 30 minutes and filtered, yielding a faint yellow solution. It was warmed to 40° C. and 10 parts of deionized water, containing 0.001 part of sodium borohydride and heated to the same temperature, was added with stirring. Upon cooling to room temperature over 2 hours, the purified THPE precipitated; it was filtered and dried and was found upon analysis to comprise 97.5% THPE and 2.5% bisphenol A.

What is claimed is:

1. A method for preparing 1,1,1-tris(4-hydroxyphenyl) ethane which comprises:

heating, at a temperature in the range of about 30°–100° C., a mixture of phenol and 2,4-pentanedione under acidic conditions and in the presence of an effective amount of a mercapto compound as promoter, the molar ratio of phenol to 2,4-pentanedione being at least about 6:1, to produce a mixture of bisphenol A and said 1,1,1-tris(4-hydroxyphenyl)ethane; and separating said 1,1,1 -tris(4-hydroxyphenyl)ethane from said bisphenol A.

2. A method according to claim 1 wherein the molar ratio of phenol to 2,4-pentanedione is at least 8:1.

3. A method according to claim 1 wherein the molar ratio of phenol to 2,4-pentanedione is above 11:1.

4. A method according to claim 1 wherein the acidic conditions are provided by the addition of hydrogen chloride gas.

5. A method according to claim 1 wherein the mercapto compound is present in the amount of about 1–5% by weight based on phenol.

6. A method according to claim 5 wherein the mercapto compound is 3-mercaptopropionic acid.

7. A method according to claim 5 wherein the mercapto compound is mercaptoacetic acid.

8. A method according to claim 1 wherein the separation step is effected by removing bisphenol A by extraction at least once with a chlorinated alkane.

9. A method according to claim 8 wherein the chlorinated alkane is methylene chloride.

10. A method according to claim 8 wherein the chlorinated alkane is 1,2-dichloroethane.

11. A method according to claim 8 wherein the extraction is performed at least twice.

12. A method for preparing and purifying 1,1,1-bis(4-hydroxyphenyl)ethane which comprises:

heating, at a temperature in the range of about 30°–100° C., a mixture of phenol and 2,4-pentanedione under acidic conditions and in the presence of an effective amount of a mercapto compound as promoter, the molar ratio of phenol to 2,4-pentanedione being at least about 6:1, to produce a mixture of bisphenol A and said 1,1,1 -tris(4-hydroxyphenyl)ethane;

combining said mixture with a chlorinated alkane in an amount to produce a precipitate of a mixture of 1,1,1-tris(4-hydroxyphenyl)ethane and bisphenol A enriched in 1,1,1-tris(4-hydroxyphenyl)ethane, and isolating said precipitate;

contacting said precipitate with a methanol-water mixture containing at least 40% methanol by volume, said methanol-water mixture being previously saturated with 1,1,1 -tris(4-hydroxyphenyl)ethane, to produce a 1,1,1-tris(4-hydroxyphenyl)ethane slurry, and recovering purified 1,1,1 -tris(4-hydroxyphenyl)ethane from said slurry.

13. A method according to claim 12 wherein the chlorinated alkane is methylene chloride.

14. A method according to claim 13 wherein said methanol-water mixture further contains a decolorizing proportion of an alkali metal borohydride or dithionite.

15. A method according to claim 14 wherein the alkali metal borohydride or dithionite is sodium borohydride.

16. A method according to claim 14 wherein the amount of said sodium borohydride in said methanol-water mixture is in the range of about 0.01–0.10% by weight.

17. A method according to claim 13 wherein methanol-water mixture separated from said purified 1,1,1-tris(4-hydroxyphenyl)ethane is recycled for contact with further precipitate.

18. A method according to claim 13 wherein said purified 1,1,1-tris(4-hydroxyphenyl)ethane is contacted with further methanol to form a solution, from which still further purified 1,1,1 -tris(4-hydroxyphenyl)ethane is precipitated by combining with water.

19. A method according to claim 18 wherein said further methanol contains a decolorizing proportion of sodium borohydride.

20. A method according to claim 18 wherein said contact with further methanol also includes contact with decolorizing charcoal.

* * * * *